United States Patent [19]

Baldwin et al.

[11] Patent Number: 4,736,064
[45] Date of Patent: Apr. 5, 1988

[54] PRODRUGS OF ANTIHYPERCHOLESTEROLEMIC COMPOUNDS

[75] Inventors: John J. Baldwin, Gwynedd Valley; Wasyl Halczenko, Hatfield; George Hartman, Lansdale, all of Pa.

[73] Assignee: Merck & Co., Inc., Rahway, N.J.

[21] Appl. No.: 912,867

[22] Filed: Sep. 29, 1986

[51] Int. Cl.$^4$ .................................. C07C 69/76
[52] U.S. Cl. .......................... 560/059; 560/60; 560/55; 560/119; 560/173; 544/171; 546/238; 546/239; 548/572; 548/573
[58] Field of Search ............... 560/59, 60, 119, 173; 544/171; 546/238, 239; 548/572, 573; 514/539, 564, 567

[56] References Cited

U.S. PATENT DOCUMENTS 4,459,422  7/1984  Willard et al. ............... 549/292
4,517,373  5/1985  Terahara et al. ............. 549/292

OTHER PUBLICATIONS

H. Bundgaard, C. Larsen, P. Thorbeck, Int. J. Pharmaceuticals, 18, 67–78, (1984), "Bundgaard (I)".
H. Bundgaard, C. Larsen, E. Arnold, Int. J. Pharmaceuticals, 18, 79–87, (1983), "Bundgaard (II)".

*Primary Examiner*—Paul J. Killos
*Attorney, Agent, or Firm*—Joseph F. DiPrima; Michael C. Sudol

[57] ABSTRACT

Prodrugs of 3-hydroxy-3-methylglutarylcoenzyme A (HMG-CoA) reductase inhibitors which are useful as antihypercholesterolemic agents and are represented by the following general structural formula (I):

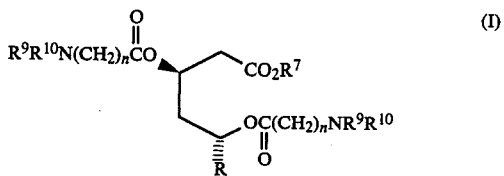

and pharmaceutically acceptable salts thereof are disclosed.

10 Claims, No Drawings

PRODRUGS OF ANTIHYPERCHOLESTEROLEMIC COMPOUNDS

BACKGROUND OF THE INVENTION

Hypercholesterolemia is known to be one of the prime risk factors for ischemic cardiovascular disease, such as arteriosclerosis. To date, there is still no effective antihypercholesterolemic agent commercially available that has found wide patient acceptance. The bile acid sequestrants seem to be moderately effective but they must be consumed in large quantities, i.e. several grams at a time and they are not very palatable.

There are agents known, however, that are very active antihypercholesterolemic agents that function by limiting cholesterol biosynthesis by inhibiting the enzyme, HMG-CoA reductase. These agents include the natural fermentation products compactin and mevinolin and a variety of semi-synthetic and totally synthetic analogs thereof.

The naturally occurring compounds and their semi-synthetic analogs have the following general structural formulae:

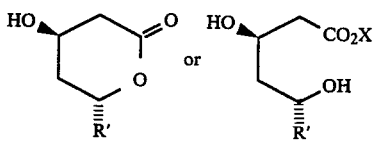

wherein
X is hydrogen, $C_{1-5}$alkyl or $C_{1-5}$alkyl substituted with a member of the group consisting of phenyl, dimethylamino or acetylamino;
R' is

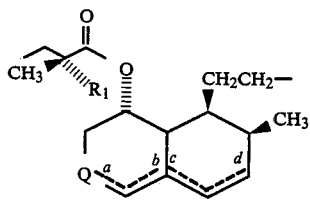

wherein
Q is

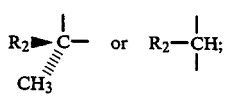

$R_2$ is hydrogen or hydroxy;
$R_1$ is hydrogen or methyl; and
a, b, c and d are single bonds, one of a, b, c and d is a double bond or a and c or b and d are double bonds provided that when a is a double bond, Q is

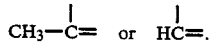

The totally synthetic antihypercholesterolemic compounds are disclosed in U.S. Pat. No. 4,375,475 and have the following general structural formulae:

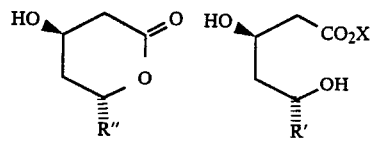

wherein R'' is:

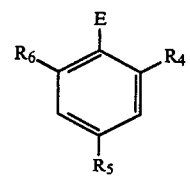

wherein:
E is $-CH_2-$, $-CH_2CH_2-$ or $-CH=CH-$;
$R_4$ and $R_5$ are independently $C_{1-3}$alkyl, fluoro, bromo or chloro; and
$R_6$ is phenyl, benzyloxy, substituted phenyl or substituted benzyloxy in which the phenyl group in each case is substituted with one or more substituents selected from $C_{1-3}$alkyl, fluoro, bromo or chloro.

SUMMARY OF THE INVENTION

This invention relates to novel compounds which are prodrugs of known HMG-CoA reductase inhibitors and which are bio-converted following systemic administration to useful antihypercholesterolemic agents. Specifically, the compounds of this invention include diaminoacyl derivatives of compactin, mevinolin, CS514, the dihydro and tetrahydro analogs thereof and the totally synthetic HMG-CoA reductase inhibitors. Additionally, pharmaceutical compositions of these prodrugs, as the sole therapeutic agent, and in combination with bile acid sequestrants are disclosed.

DETAILED DESCRIPTION OF THE INVENTION

The specific prodrugs of this invention are the compounds represented by the following general structural formula (I):

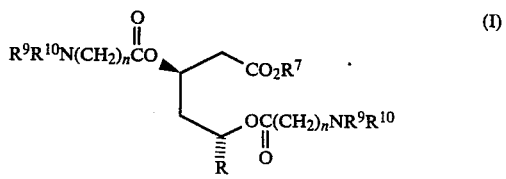

wherein:
n is 1 to 6;
R is selected from a group consisting of:

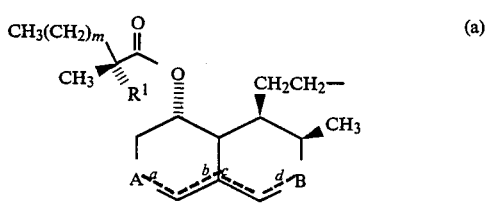

wherein:

m is 1 to 5;
R$^1$ is hydrogen or methyl;
A is

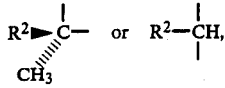

in which R$^2$ is hydrogen or hydroxyl;
B is

in which R$^3$ is hydrogen or hydroxyl;
a, b, c and d represent single bonds, one of a, b, c and d represents a double bond or both a and c or both b and d represent double bonds, provided that when a is a double bond, A is

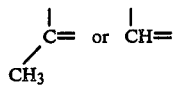

and when d is a double bond, B is

or

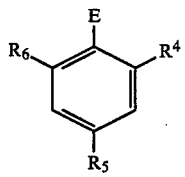

(b)

wherein:
E is —CH$_2$—; —CH$_2$CH$_2$— or —CH=CH—;
R$^4$ and R$^5$ are independently C$_{1-3}$alkyl, fluoro, bromo or chloro; and
R$^6$ is phenyl, benzyloxy, substituted phenyl or substituted benzyloxy in which the phenyl group in each case is substituted with one or more substituents selected from C$_{1-3}$alkyl, hydroxy-C$_{1-3}$alkyl, fluoro, bromo or chloro;
R$^7$ is hydrogen or C$_{1-8}$alkyl;
R$^9$ and R$^{10}$ independently are hydrogen, or C$_{1-8}$alkyl or when taken together with the nitrogen atom to which they are attached form a heterocycle selected from the group consisting of piperidinyl, pyrrolidinyl, or morpholinyl;
and pharmaceutically acceptable salts thereof.

One embodiment of this invention are the compounds of the formula (I) wherein R is the group (b). Illustrative of this embodiment are compounds wherein E is —CH=CH—; R$^4$ and R$^5$ are independently C$_{1-3}$alkyl and R$^6$ is substituted phenyl. More specifically, group (b) is:

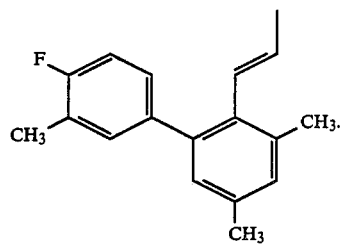

Exemplifying this embodiment are the class of compounds wherein R$^9$ and R$^{10}$ are independently hydrogen or C$_{1-8}$alkyl and specifically, ethyl (E)-7-(4'-fluoro-3,3',5-trimethyl-[1,1'-biphenyl]-2-yl)-3(R),5(S)-bis(N,N-dimethylaminoacetoxy)-hept-6-enoate.

A second embodiment of this invention are the compounds of the formula (I) wherein R is the group (a).

The pharmaceutically acceptable salts are those acid addition salts of non-toxic, pharmaceutically acceptable acids and include salts of inorganic acids such as hydrochloric, hydrobromic, hydroiodic, phosphoric, sulfuric, nitric and the like, and organic acids such as trifluoroacetic, trichloroacetic, acetic, oxalic, maleic and the like and include acids related to the pharmaceutically acceptable salts listed in Journal of Pharmaceutical Science, 66, 2 (1977) and incorporated herein by reference.

The compounds of this invention are conveniently prepared from known HMG-CoA reductase inhibitors according to the following synthetic pathway:

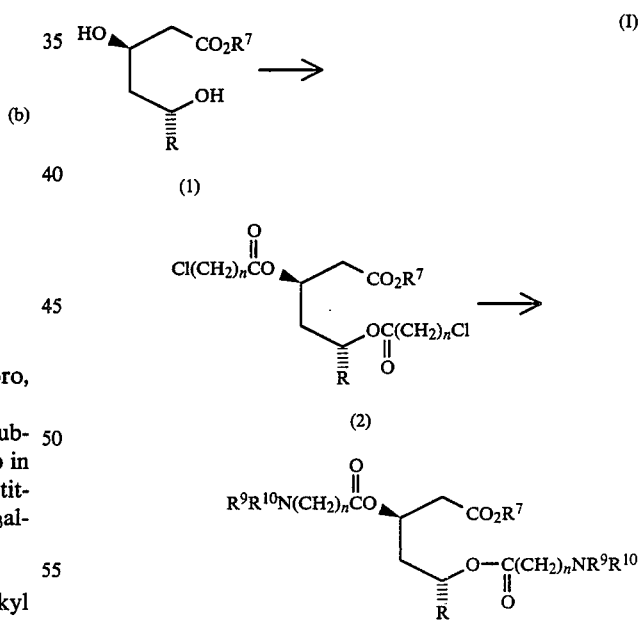

The compounds of the formula (1) are known in the art. When R is the group (a), the compounds of the formula (1) are the C$_{1-8}$ alkyl esters of the free hydroxy acid form of compactin, mevinolin, CS514 and their dihydro and tetrahydro analogs which are readily available or may be prepared according to the fermentation procedures disclosed in U.S. Pat. Nos. 3,983,140; 4,049,495; 4,231,938; 4,294,846 and 4,517,373 and the hydrogenation procedures disclosed in U.S. Pat. No. 4,351,844. When R is the group (b), the compounds of the formula (1) are readily available by utilizing the procedures described in U.S. Pat. No. 4,375,475.

The compounds of the formula (1) are reacted with the appropriate haloalkylacylhalide, hal(CH$_2$)$_n$COhal, where n is described above and hal is chloro or bromo, such as chloroacetyl chloride, in the presence of a molecular equivalent of an acid acceptor, such as trialkylamine, specifically trimethylamine, triethylamine, pyridine, N,N-dimethylbenzylamine and the like to afford the compounds of the formula (2). The compounds of the formula (2) are then reacted with two molecular equivalents of a secondary amine of the formula HNR$^9$R$^{10}$, such as dimethylamine, diethylamine, piperidine and the like to form the compounds of the formula (I).

For the compounds of the formula (I) which contain a primary or secondary alcohol functionality, the above described process is modified as follows. The hydroxyl groups in the 3- and 5-position of the dihydroxy ester moiety of compound (1) are selectively protected by the formation of an acetal, ketal and the like. For example a dimethyl ketal may be formed by utilizing acetone. The primary or secondary alcohol function is then converted to a silyl ether. For example, a trialkyl silyl ether may be formed by utilizing t-butyldimethylsilyl halide. Then the hydroxyl groups in the 3- and 5-position of the dihydroxy ester moiety are reformed by the selective removal of the acetal, ketal or the like protecting group. The resultant compounds of the formula (1) wherein the primary or secondary alcohol function is protected as a silyl ether is then treated according to the above synthetic pathway which after the selective removal of the silyl ether protecting group give the compounds of formula (I).

The compounds of this invention are useful as prodrugs of antihypercholesterolemic agents for the treatment of arteriosclerosis, hyperlipidemia, familial hypercholesterolemia and the like diseases in humans. They may be administered orally in the form of a capsule, a tablet, or the like. Doses may be varied, depending on the age, severity, body weight and other conditions of human patients but daily dosage for adults is within a range of from about 20 mg to 2000 mg (preferably 20 to 100 mg) which may be given in two to four divided doses. Higher doses may be favorably employed as required.

The compounds of this invention may also be coadministered with pharmaceutically acceptable nontoxic cationic polymers capable of binding bile acids in a non-reabsorbable form in the gastro-intestinal tract. Examples of such polymers include cholestyramine, colestipol and poly[methyl-(3-tri-methylaminopropyl-)imino-trimethylene dihalide]. The relative amounts of the compounds of this invention and these polymers is between 1:100 and 1:15,000.

The ability of the compounds of this invention to act as prodrugs of antihypercholesterolemic agents is demonstrated in a standard in vivo pharmacological assay in dogs.

Eight male beagle dogs weighing from 7.2–12.9 kilograms approximately 4–5 years old were fed a low cholesterol, semi-synthetic diet once a day in the morning in sufficient quantity to maintain a constant body weight. The animals were trained to consume their entire ration each day. Cholestyramine, 12 g, was administered daily in the diet. This amount routinely resulted in an average reduction in plasma total cholesterol of approximately 35%. Dogs were bled twice a week from the jugular vein and plasma cholesterol was determined after extraction and saponification by a colorimetric procedure (Liebermann Burchard). After the establishment of pretreatment plasma cholesterol levels, one or more dogs were treated with a daily dose of test compound mixed directly into the diet for 14 days.

Representative of the pharmacological activity of the compounds of this invention, ethyl (E)-7-(4'-fluoro-3,3',5-trimethyl-[1,1'-biphenyl]-2-yl)-3(R),5(S)-bis(N,N-dimethylaminoacetoxy)-hept-6-enoate as the dioxalate salt at a dosage of 8 mg/kg/day over 14 days reduced plasma cholesterol by 28 percent.

Included within the scope of this invention is the method of treating arteriosclerosis, familial hypercholesterolemia or hyperlipidemia which comprises administering to a subject in need of such of the compounds of formula (I) or pharmaceutical compositions thereof.

The following examples illustrate the preparation of the compounds of the formula (I) and their incorporation into pharmaceutical compositions and as such are not to be considered as limiting the invention set forth in the claims appended hereto.

EXAMPLE 1

Preparation of Ethyl
(E)-7-(4'-Fluoro-3,3',5-trimethyl-[1,1'-biphenyl]-2-yl)-3(R),5(S)-bis(N,N-dimethylaminoacetoxy)-hept-6-enoate dioxalate salt (a)

Ethyl
(E)-7-(4'-Fluoro-3,3',5-trimethyl-[1,1'-biphenyl]-2-yl)-3(R),5(S)-bis(chloroacetoxy)-hept-6-enoate (1a)

To a solution of 0.25 g (0.62 mmol) ethyl (E)-7-(4'-fluoro-3,3',5-trimethyl-[1,1'-biphenyl]-2-yl)-3(R),5(S)-dihydroxyhept-6-enoate and 0.15 g (1.86 mmol) pyridine in 15 ml CH$_2$Cl$_2$ under nitrogen at room temperature was added dropwise a solution of 0.2 g (1.86 mmol) chloroacetylchloride with stirring. After 1.0 hours at room temperature, the reaction mixture was diluted with 25 ml CH$_2$Cl$_2$ and then was washed successively with H$_2$O, dilute aqueous hydrochloric acid, H$_2$O, brine. This solution was dried and the solvent removed in vacuo to give the crude product as an oil. This was purified by flash chromatography on silica gel eluting with 3% isopropanol/hexane to provide pure (1a) as a clear oil.

(b)

Ethyl
(E)-7-(4'-Fluoro-3,3',5'-trimethyl-[1,1'-biphenyl]-2-yl)-3(R),5(S)-bis(N,N-dimethylaminoacetoxy)-hept-6-enoate (1b)

To 6.8 g (12.3 mmol) the compound (1a) in 30 ml CH$_2$Cl$_2$ cooled to 0°–5° C. under nitrogen was added dropwise a solution of 2.25 g (50 mmol) dimethylamine in 30 ml CH$_2$Cl$_2$ over 0.5 hours and the resulting solution allowed to gradually come to room temperature over 6 hours. The reaction mixture was then diluted with 40 ml CH$_2$Cl$_2$ and this was washed with 3×25 ml H$_2$O, dried and the solvent removed in vacuo to provide crude product. This was purified by flash chromatography on silica gel eluting with 7% methanol/chloroform to give pure (1b) as an oil.

(c)

Ethyl
(E)-7-(4'-Fluoro-3,3',5'-trimethyl-[1,1'-biphenyl]-2-yl)-3(R),5(S)-bis(N,N-dimethylaminoacetoxy)-hept-6-enoate dioxalate salt To the compound (1b) dissolved in acetone (15 ml) at ambient temperature was added oxalic acid (2 molar equivalents) to give a white solid. The white solid was filtered off, triturated with acetone and dried to yield the desired compound. m.p. 152°–154° C.

Anal. Calc'd for $C_{36}H_{47}FN_2O_{14}$: C, 57.59; H, 6.31; N, 3.73. Found: C, 57.61; H, 6.52; N, 3.94.

In a similar fashion the dimaleate salt was prepared. m.p. 116°–8° C.

Anal. Calc'd for $C_{40}H_{51}FN_2O_{14}$: C, 59.84; H, 6.40; N, 3.49. Found: C, 60.22; H, 6.50; N, 3.52

EXAMPLE 2

Preparation of Isopropyl
(E)-7-(4'-Fluoro-3,3',5-trimethyl-[1,1'-biphenyl]-2-yl)-3(R),5(S)-bis(N,N-dimethylaminoacetoxy)-hept-6-enoate bismaleate salt Utilizing the general procedures in Example 1 the above titled compound was prepared. m.p. 120°–122° C.

Anal. Calc'd for $C_{41}H_{53}FN_2O_{14}$: C, 60.28; H, 6.54; N, 3.43. Found: C, 60.27; H, 6.78; N, 3.23

EXAMPLES 3–6

Utilizing the general procedures in Example 1 the following compounds are prepared:

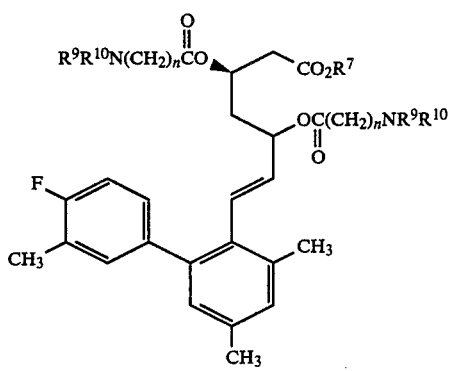

| Compound No. | n | $R^7$ | $R^9$ | $R^{10}$ |
|---|---|---|---|---|
| 3 | 2 | Me | Et | Et |
| 4 | 3 | i-Bu | —CH$_2$CH$_2$CH$_2$CH$_2$— | |
| 5 | 4 | n-Hex | —CH$_2$CH$_2$OCH$_2$CH$_2$— | |
| 6 | 6 | H | Me | Me |

EXAMPLES 7–9

Utilizing the general procedure in Example 1 the following compounds are prepared:

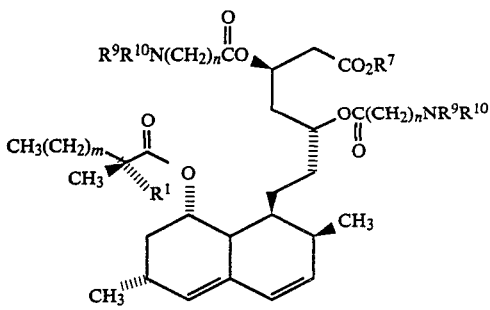

| Compound No. | m | n | $R^1$ | $R^7$ | $R^9$ | $R^{10}$ |
|---|---|---|---|---|---|---|
| 7 | 1 | 2 | H | Me | Et | Et |
| 8 | 2 | 3 | Me | i-Bu | —CH$_2$CH$_2$CH$_2$CH$_2$— | |
| 9 | 1 | 4 | Me | H | —CH$_2$CH$_2$OCH$_2$CH$_2$— | |

EXAMPLE 10

As a specific embodiment of a composition of this invention, 40 mg of the compound of Example 1 is formulated with sufficient finely divided lactose to provide a total amount of 580 to 590 mg to fill a size 0 hard gelatin capsule.

What is claimed is:

1. A compound represented by the general structural formula (I):

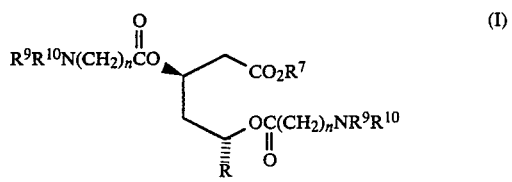

wherein:
n is 1 to 6;
R is selected from a group consisting of:

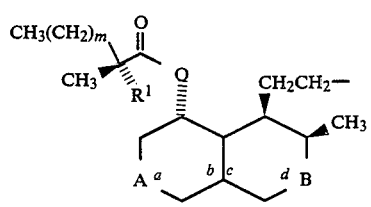

wherein:
m is 1 to 5;
$R^1$ is hydrogen or methyl;
A is

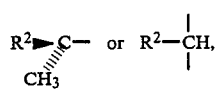

in which $R^2$ is hydrogen or hydroxyl;
B is

in which $R^3$ is hydrogen or hydroxyl;

a, b, c and d represent single bonds, one of a, b, c and d represents a double bond or both a and c or both b and d represent double bonds, provided that when a is a double bond, A is

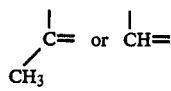

and when d is a double bond, B is

or

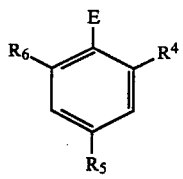 (b)

wherein:

E is —$CH_2$—, —$CH_2CH_2$— or —CH=CH—;

$R^4$ and $R^5$ are independently $C_{1-3}$ alkyl, fluoro, bromo or chloro; and $R^6$ is phenyl, benzyloxy, substituted phenyl or substituted benzyloxy in which the phenyl group in each case is substituted with one or more substituents selected from $C_{1-3}$alkyl, hydroxy-$C_{1-3}$alkyl, fluoro, bromo or chloro;

$R^7$ is hydrogen or $C_{1-8}$alkyl;

$R^9$ and $R^{10}$ independently are hydrogen or $C_{1-8}$alkyl or when taken together with the nitrogen atom to which they are attached form a heterocycle selected from the group consisting of piperidinyl, pyrrolidinyl, or morpholinyl;

or a pharmaceutically acceptable salt thereof.

2. A compound of claim 1 wherein R is the group (b).

3. A compound of claim 2 wherein E is —CH=CH—.

4. A compound of claim 3 wherein: $R^4$ and $R^5$ independently are $C_{1-3}$alkyl; $R^6$ is a substituted phenyl; and n is 1 to 3.

5. A compound of claim 4 wherein R is:

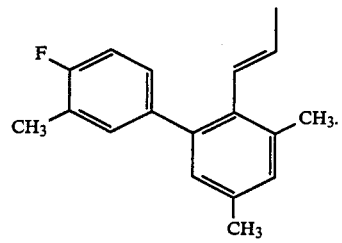

6. A compound of claim 5 wherein: $R^9$ and $R^{10}$ are independently hydrogen or $C_{1-8}$alkyl.

7. A compound of claim 6 which is ethyl (E)-7-(4'-fluoro-3,3',5-trimethyl-[1,1'-biphenyl]-2-yl)-3(R),5(S)-bis(N,N-dimethylaminoacetoxy)-hept-6-enoate or a pharmaceutically acceptable salt thereof.

8. A compound of claim 7 which is the dioxalate salt.

9. A hypocholesterolemic, hypolipidemic pharmaceutical composition comprising a nontoxic therapeutically effective amount of a compound of claim 1 and a pharmaceutically acceptable carrier.

10. A method of inhibiting cholesterol biosynthesis comprising the administration to a subject in need of such treatment a nontoxic therapeutically effective amount of a compound of claim 1.

* * * * *